United States Patent
Depfenhart et al.

(10) Patent No.: US 11,357,536 B2
(45) Date of Patent: Jun. 14, 2022

(54) DEVICE AND METHOD FOR PRODUCING A MICRO-GRAFT MATRIX FROM FULL-THICKNESS SKIN

(71) Applicant: LAVENIR BIOSCIENCE AG, Hamburg (DE)

(72) Inventors: Markus Depfenhart, Hamburg (DE); Jörg Müller, Buchholz (DE); Hoc-Kiem Trieu, Berlin (DE); Matthias Spanic, Berlin (DE)

(73) Assignee: LA VENIR BIOSCIENCE AG, Hamburg (DE)

( * ) Notice: Subject to any disclaimer, the term of this patent is extended or adjusted under 35 U.S.C. 154(b) by 342 days.

(21) Appl. No.: 16/496,399

(22) PCT Filed: Feb. 22, 2018

(86) PCT No.: PCT/EP2018/054404
§ 371 (c)(1),
(2) Date: Sep. 20, 2019

(87) PCT Pub. No.: WO2018/172015
PCT Pub. Date: Sep. 27, 2018

(65) Prior Publication Data
US 2021/0401447 A1 Dec. 30, 2021

(30) Foreign Application Priority Data
Mar. 23, 2017 (DE) ...................... 10 2017 106 310.2

(51) Int. Cl.
*A61B 17/322* (2006.01)
*A61B 17/00* (2006.01)

(52) U.S. Cl.
CPC .. *A61B 17/322* (2013.01); *A61B 2017/00004* (2013.01); *A61B 2017/00402* (2013.01);
(Continued)

(58) Field of Classification Search
CPC .............. A61B 17/322; A61B 17/3205; A61B 17/32053; A61B 17/3209;
(Continued)

(56) References Cited

U.S. PATENT DOCUMENTS

| 4,270,540 A | 6/1981 | Schwartz |
| 2011/0125187 A1* | 5/2011 | Soltz ........................ A61P 43/00 606/214 |

(Continued)

FOREIGN PATENT DOCUMENTS

| WO | 2016033584 A1 | 3/2016 |
| WO | 2018172015 A1 | 9/2018 |

OTHER PUBLICATIONS

"PCT Search Report issued in PCT/EP2018/054404", dated May 22, 2018, 6 pages.

*Primary Examiner* — Katherine M Shi
*Assistant Examiner* — Paige A Codrington
(74) *Attorney, Agent, or Firm* — Johnson, Marcou, Isaacs & Nix, LLC

(57) ABSTRACT

A device set and a method for producing a micro-graft matrix with a plurality of punched full-thickness skin parts (12) from skin includes a film set of at least one first film (1) and one second film (2), which adhere to and are peelable from one another; an adhesive (10) to stick the first film (1) onto the skin; a cutting device with an adapter to provide a predefined distance to the skin and to make a plurality of hollow-cylindrical cuts vertical to the film set down to a predetermined depth in the skin underneath, the film set being respectively cut and divided, so that an outer portion of the second film can be peeled off and inner portions remain; and a third film (3), stuck in contact with the second
(Continued)

film (2). The punched full-thickness skin parts can be extracted from the skin as the micro-graft matrix using the third film (3).

45 Claims, 10 Drawing Sheets

(52) U.S. Cl.
CPC .............. *A61B 2017/00995* (2013.01); *A61B 2017/3225* (2013.01)

(58) Field of Classification Search
CPC .... A61B 17/32093; A61B 2017/00004; A61B 2017/00995; A61B 2017/3225; A61B 2017/00752; A61B 2017/00747; A61B 2017/00876; A61B 2017/00526; A61B 2017/00402; A61M 37/0015
USPC ........................................................ 606/132
See application file for complete search history.

(56) References Cited

U.S. PATENT DOCUMENTS

| | | | |
|---|---|---|---|
| 2011/0313429 A1* | 12/2011 | Anderson | A61B 10/0233 606/131 |
| 2014/0081251 A1 | 3/2014 | Giovannoli | |
| 2016/0015416 A1* | 1/2016 | Franco | A61B 17/32053 606/132 |

* cited by examiner

DEVICE AND METHOD FOR PRODUCING A MICRO-GRAFT MATRIX FROM FULL-THICKNESS SKIN

CROSS REFERENCE TO RELATED APPLICATIONS

The instant application should be granted the priority dates of Feb. 22, 2018, the filing date of the international patent application PCT/EP2018/054404 and Mar. 23, 2017, the filing date of German Patent Application DE 10 2017 106 310.2.

BACKGROUND OF THE INVENTION

The present invention relates to a device set for producing a micro-graft matrix from full-thickness skin comprising a film set with a first and a second film, which are coplanar, adhere to one another and are peelable from one another, a cutting device, by means of which a plurality of hollow-cylindrical cuts are made through the film set sticking to the skin and into the skin, and a third film forming an adhesive bond with the second film.

Various devices and methods for producing a micro-graft matrix or transplantation matrix from full-thickness skin or split-thickness skin comprising an upper skin are known as the state of the art. Split-thickness skin parts comprising the epidermis and the upper papillary, but not the reticular dermis, however, are by far less effective for transplantation than full-thickness skin parts or punched full-thickness skin parts. For producing the micro-graft matrix or transplantation matrix from healthy skin, the following requirements are of key importance: low morbidity of the donor skin area, low morbidity of the removed skin parts, minimal stress on the patient, and fastest possible method.

US 2014 0277 454 A1 discloses a device and a method, in which a plate with a plurality of holes or indentations is applied onto the skin, wherein the holes are interconnected by channels and a vacuum is applied thereto. With the vacuum applied, a plurality of skin parts are drawn out into the holes or indentations and can be cut off or peeled off. In this manner, however, only split-thickness skin is removed.

In Phlebologie 2016; 45: p. 100-105, Schattauer-Verlag (http://dx.doi.org/10.12687/phleb2303-2-2016) with the title "Plastic chronic wound management with Cellutome", G. U. Seip discloses a device and a method similar to US 2014 0277 454 A1, by means of which skin elevations produced in a first step can be covered with an adhesive film, and then, adhering to the film, can be cut off, removed and transplanted in a second step.

US 2014 0 277 454 A1 discloses a device and a method, in which, using a plate with a plurality of holes, a plurality of skin parts is removed from the donor skin area to then be applied onto a recipient skin area. A housing is arranged above the plate, surrounding a rear side of the plate and sealing it against the respective skin area, so that tissue fluid can be sucked out and distributed through channels introduced into the plate.

US 2015 0 238 212 A1 discloses various methods, by means of which devices for producing the micro-graft matrix or transplantation matrix from full-thickness skin or split-thickness skin can be manufactured.

US 2014 039 523 A1 discloses a device and a method, in which, using a needle roller with a plurality of hollow needles, skin parts are punched out from the skin upon rolling it over the skin. With the needle roller, punched split-thickness skin parts as well as punched full-thickness skin parts can be removed; however, removing and using the punched full-thickness skin parts from the needles is extremely laborious to impossible. The needle roller is intended for skin perforation rather than for skin removal for the purpose of transplantation.

Similar to the method according to US 2014 039 523 A1, but much more complex in terms of equipment, micro-punches are known, by means of which punched split-thickness and full-thickness skin parts can be sequentially removed from skin in the form of a matrix, which then, however, must be further processed individually for the purpose of transplantation. Such a method is very complex in terms of equipment as well as very time-consuming.

DE 10 2009 018 940 A1 discloses a device with a hollow punch having a cutting edge with a jagged outline shape, so that the skin is respectively cut out in a star shape in order to blur the outline shape on the skin following punching out. With that, larger skin areas can also be punched or cut and then peeled off.

In general, in conjunction with this patent application, punching shall always mean unilateral punching into the skin from above or vertical cutting into the skin from above, in order to then be able to lift off a skin part or punched skin part thus produced and, preferably, to transplant it.

The known methods only allow for relatively limited skin removal of 2-3% of the body surface, which often is too little for a therapy on larger wound surfaces, such as, for example, extensive burns. This also often leads to undesired subsequent scarring.

SUMMARY OF THE INVENTION

In order to eliminate the disadvantages from the state of the art, the object of the invention therefore consists in providing a device set for producing a micro-graft matrix from full-thickness skin, which can be produced with the least amount of equipment as possible, as fast as possible, with as few donor site defects as possible, and across a skin removal area as large as possible.

According to the invention, a device set for producing a micro-graft matrix with a plurality of punched full-thickness skin parts from skin of a skin removal area is provided, comprising the following components:

a film set with a predetermined thickness of at least one first film and one second film, wherein the first film is designed to be stuck onto the skin with a flat lower side and to adhere, with an opposite upper side, to a lower side of the second film in a coplanar fashion with a second adhesive strength and to be peelable from one another;

an adhesive to stick the lower side of the first film onto the skin, wherein a first adhesive strength is created between the lower side of the first film and the skin, which is higher than the second adhesive strength, so that the second film is peelable from the first film sticking to the skin;

a cutting device with an adapter, which is designed, by pressing it onto the film set sticking to the skin, to provide a predefined distance to the skin underneath in the skin removal area considering the thickness of the film set, wherein the cutting device is designed to make a plurality of hollow-cylindrical cuts in parallel to one another with respectively one inner diameter of the hollow cylinders and one hollow cylinder distance from one another vertical to the film set and down to a predetermined depth in the skin underneath, so that the plurality of the hollow-cylindrical cuts are made in the skin removal area in the form of a matrix, in order to divide the film set by the hollow-cylindrical cuts into respective inner portions with a respective inner portion of the second film located above the respectively cut punched full-thickness skin part and into a respective outer portion with an outer portion of the second film; and a third film having a size at least as large as the removal area and being designed, in contact with an upper side of the second film opposite the lower side of the second film, to create a third adhesive strength, wherein the first, second and third adhesive strengths are higher than a fourth adherence, with which the punched full-thickness skin parts are held in the skin.

The inventive device set is particularly simple and cost-effective and can be quickly applied, since the plurality of punched full-thickness skin parts produced therewith can be jointly connected with the third film in a simple manner and thus jointly removed. Thus, an entire matrix of punched full-thickness skin parts, which represents the micro-graft matrix, can be removed in one operation. The film set with the first and second films is simple and cost-effective and can be easily stuck onto the skin, which is a donor skin. By making vertical, hollow-cylindrical cuts down to the predetermined depth of the skin with the application of the device set with the cutting device, first, the film set of the first and second films also is cut along the cutting line. Thereby, inner portions and an outer portion of the first and the second film are produced. When the cuts are made down to the predetermined depth of the skin, the punched, full-thickness skin parts are produced with a cylindrical shape. The punched full-thickness skin parts are connected with the respective inner portion of the first and the second film, but they are not connected with the rest of the film set, so that they can be extracted together with the respective inner portions of the first film and the second film above it. Peeling off the remaining outer portion of the second film, located outside the annular cuts into the skin, from the first film, the inner portions of the second film are now elevated with respect to the first film, with voids therebetween. This is easily identifiable in FIG. 7. Now the third film can be simply applied onto the elevated inner portions of the second film and adhered thereto. Upon subsequent peeling off of the third film from the skin, the punched full-thickness skin parts are extracted as the micro-graft matrix. Thus, with the inventive device set, the plurality of punched full-thickness skin parts can be held in their position to one another and the axial orientation obtained and extracted from the skin by their adhesion to the third film. Advantageously, then, not every punched skin part must be transplanted by itself, but the matrix of the punched full-thickness skin parts or the "micro-graft matrix" as a whole can be placed on the wound to be treated and adhered thereto. Then, the punched skin parts can take root in the wound and mature therebetween. The inventive device set thus enables a much shorter treatment period and a much lower morbidity than would be possible with devices and methods according to the state of the art.

The advantages achieved with the invention particularly consist in the fact that, with the combination of simple and cost-effective means, particularly good, fast and extensive full-thickness skin removal is enabled.

With the plurality of punched full-thickness skin parts at suitable distances from one another, the inventive device set and method also enable their removal across large skin removal areas. Thus, an overall donor area of 2-3% of the body surface, as in the state of the art, can now be extended to 20-50%, whereby the morbidity of patients is drastically reduced.

Scarring is likewise avoided completely, since the skin in the donor area is not removed continuously over large areas, but only in a micro-fractional and partial fashion through the plurality of cavities spaced from one another, which result from the removal of the punched full-thickness skin parts. It is known that full-thickness skin defects having a diameter of less than or equal to 300 micrometers principally heal without scarring. Thus, after the generation of defects with the inventive device set, the skin can rejuvenate naturally and regrow without scarring (restitutio ad integrum). In the wound area, too, where the punched full-thickness skin parts are transplanted to, the skin between the punched full-thickness skin parts can mature well.

It is also advantageous that punched skin parts, for example, can be removed and transplanted with hair and other reticular dermal skin components, and in this manner a hair transplant can be performed as well.

Preferably, the cutting device is a support plate with a plurality of hollow micro-punches arranged in the form of a matrix. Thus, many cuts can be made at once and cost-effectively.

As a preferred alternative, a laser having an optical system is used as the cutting device, making the plurality of cuts down to the predetermined depth.

Further advantages can be retrieved from the detailed description.

BRIEF DESCRIPTION OF THE DRAWINGS

Preferred embodiments according to the present invention are represented in the subsequent drawings and in a detailed description, however, they are not intended to limit the present invention thereto exclusively.

The Figures Show.

DETAILED DESCRIPTION OF EMBODIMENTS

Figure 1:
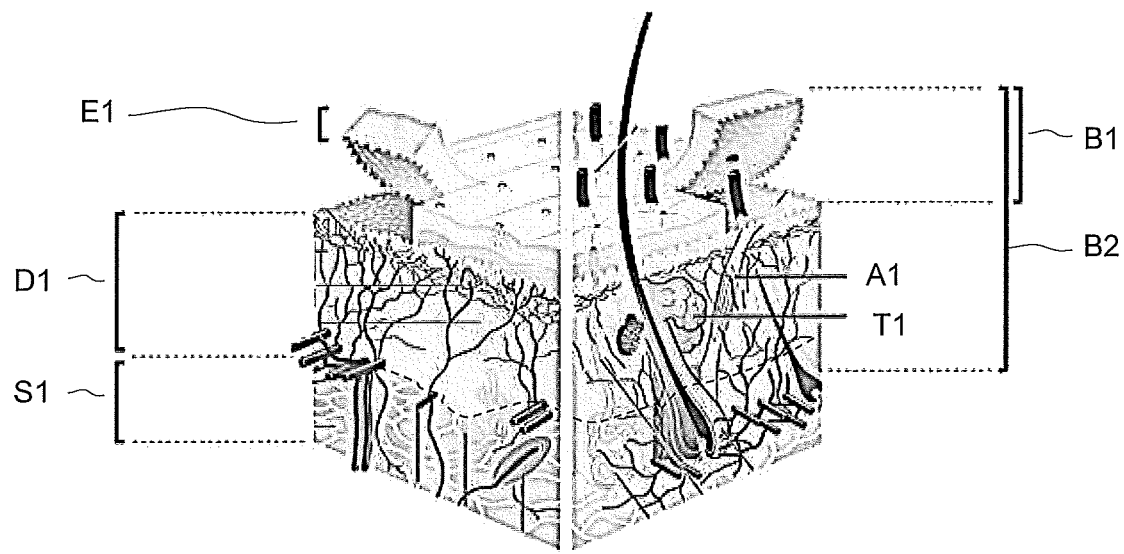
FIG. 1 a perspective view of a sectional image of human skin with epidermis, reticular dermis and subcutis.

FIG. 1 shows a perspective view of a sectional image of human skin with epidermis E1, dermis D1 and subcutis S1. According to the state of the art, mostly only areas of the split-thickness skin B1 are cut or punched out from a skin removal area.

Upon skin removal for transplantation, areas of the full-thickness skin B2 that may also contain skin appendages like hair, sweat glands A1, sebaceous glands T1, receptors and skin nerves are more desired.

As indicated above, with the inventive device set and method for producing a micro-graft matrix of punched full-thickness skin parts 12 from skin of a skin removal area, a much larger transplant can be achieved without scarring. With a removal of a plurality of punched full-thickness skin parts and with suitable distances of the punched full-thickness skin parts to one another, a donor area of 2-3% of the body surface, as in the state of the art, can now be extended to 20-50%.

In general, the inventive device set for producing the micro-graft matrix comprises the following components:

a) a film set with a predetermined thickness of at least one first film 1 and one second film 2. The first film 1 is designed in a flat fashion, in order to be stuck onto the skin with a flat first lower side. A first upper side opposite the first lower side is coplanar to a second lower side of the second film 2 and adheres thereto with a second adhesive strength, wherein the second film 2, however, is peelable from the first film 1.

b) an adhesive 10 to stick the first lower side of the first film 1 onto the skin, wherein a first adhesive strength is created between the first lower side of the first film 1 and the skin. The first adhesive strength is higher than the second adhesive strength, so that the second film 2 is peelable from the first film 1 sticking to the skin.

In general, a physical quantity, which is indicated in N/cm², is seen as the adhesive strength or adherence. In this regard, Lateral friction forces of the punched full-thickness skin parts in the skin, which are laterally cut in a cylinder shape, may also provide a component to the respective adhesive strength or adherence.

c) a cutting device with an adapter, wherein the adapter is designed, by pressing it onto the film set sticking to the skin, to provide a predefined distance to the skin underneath in the skin removal area considering the thickness of the film set. The predetermined distance of the adapter to the skin, which actually means the skin surface, preferably corresponds to the thickness of the film set. With common low contact pressures onto the skin, the film set is essentially assumed to be incompressible, so that it maintains its thickness. In this connection, the contact pressure may lie in a range of 0.01-1 N/cm² or higher.

Figure 8:
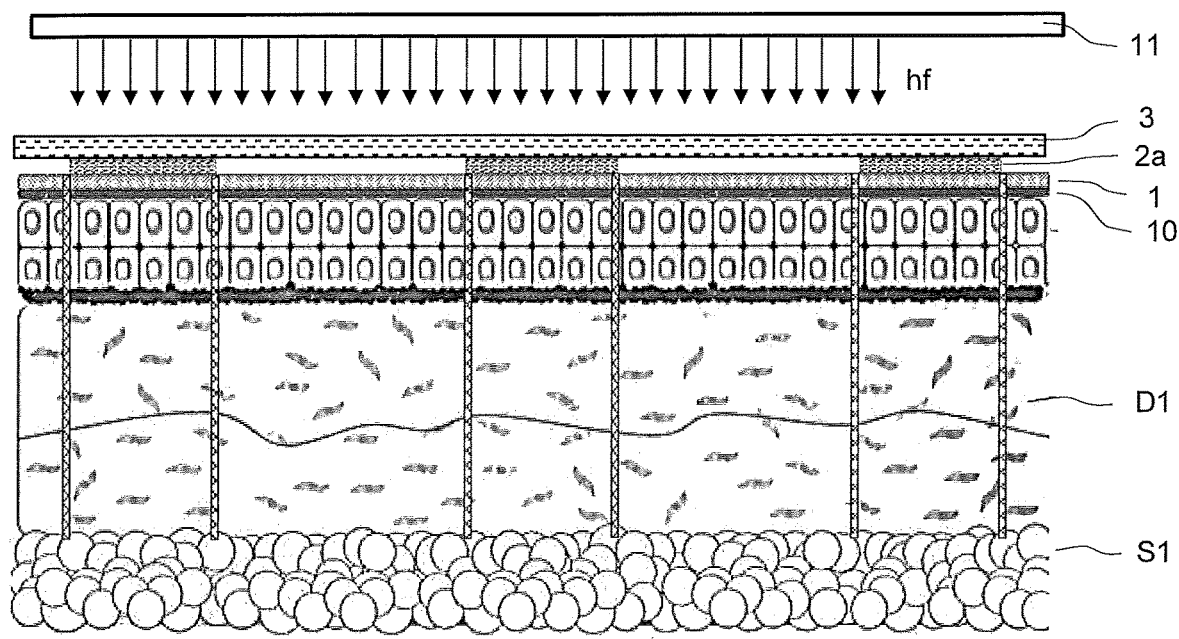
FIG. 8 a lateral sectional image of the skin with the film set of FIG. 7, wherein the outer portion of the second film has been peeled off from the first film and a third film has been applied onto the inner portions of the second film and is irradiated with light from a light source.
Figure 9:
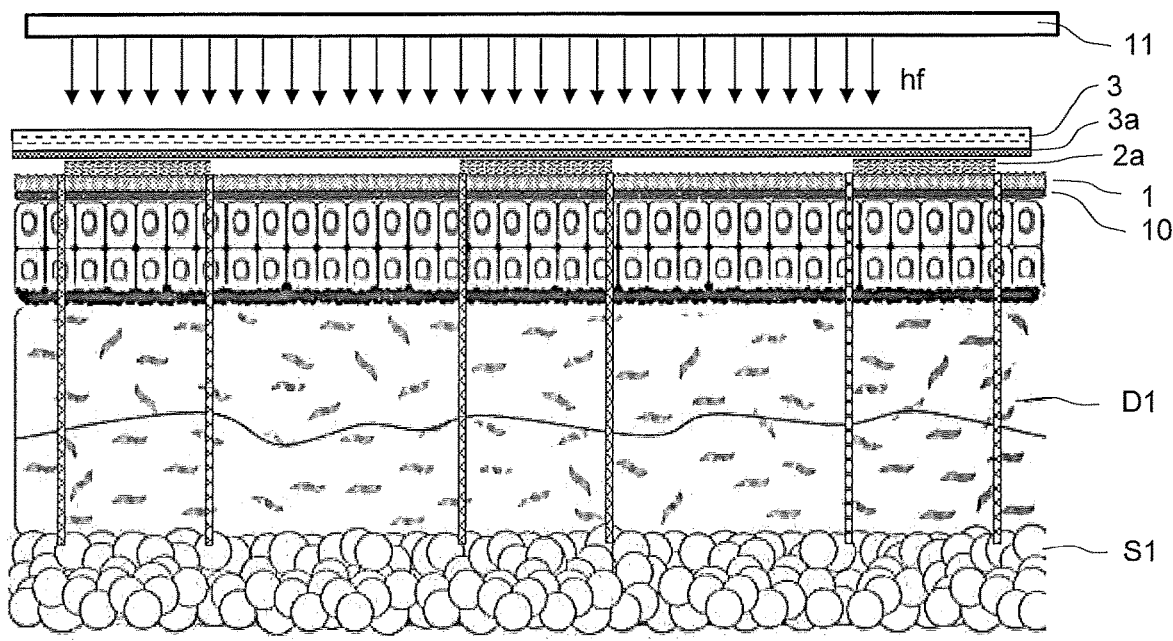
FIG. 9 a lateral sectional image of the skin with the first, second and third films and the light source of FIG. 8, wherein a second adhesive layer has been introduced between the second film and the third film.

The cutting device, therefore, is designed to make a plurality of hollow-cylindrical cuts in parallel to one another with respectively one inner diameter of the hollow cylinders and one hollow cylinder distance to one another vertical to the film set and down to a predetermined depth in the skin underneath. The plurality of hollow-cylindrical cuts are made in the form of a matrix distributed across the skin removal area. The hollow-cylindrical cuts, which are made vertical to the film set and into the skin, have the respective hollow cylinder distance to the adjacent cuts, which may also vary between the cuts. For example, round cutting lines, which result from the hollow-cylindrical cuts on the film set and on the skin surface, may be distributed in a checkerboard pattern or honeycomb-like pattern or differently. With the hollow-cylindrical cuts, or for brevity's sake, referred to as "cuts", the film set is subdivided into respective inner portions and one respective outer portion. The second film is subdivided into respective inner portions 2a respectively located above the respective punched full-thickness skin part 12 and into one outer portion 2b, from which the inner portions 2a are cut out. Since the inner portions 2a are spaced from one another, the outer portion 2b of the second film remains contiguous.

d) a third film 3 having a size at least as large as the removal area. The third film 3 is designed, in contact with an upper side of the second film 2 opposite the second lower side of the second film 2, to create a third adhesive strength. The third adhesive strength can be created by simple contact of the films or the respective surfaces of the films with one another, or, for example, by means of a first light radiation hf from a first light source 11, as shown in FIGS. 8 and 9. Alternatively, the bonding or the third adhesive strength can be achieved by interlinking and/or adhesion of the second film 2 with the third film 3. For this purpose, the second film 2 and the third film 3 are respectively designed to produce such an interlinking or adhesion with one another.

It is important that the first, second and third adhesive strengths are higher than a fourth adherence, with which the respectively cut punched full-thickness skin parts 12 are held in the skin. The fourth adherence is in part created by lateral friction of the respective punched full-thickness skin part 12 in the skin and in part by adherence of the respective punched full-thickness skin part 12 to a bottom end, which has not been cut through. The fourth adherence may also be understood as the lifting strength, which is required to extract the punched full-thickness skin part from the skin. Since the first 1, second 2 and third film 3 and the adhesive 10 are designed such that the first, second and third adhesive strengths are higher than the fourth adherence, the respectively cut punched full-thickness skin parts 12 can be extracted from the skin, which is a donor skin.

Figure 2:
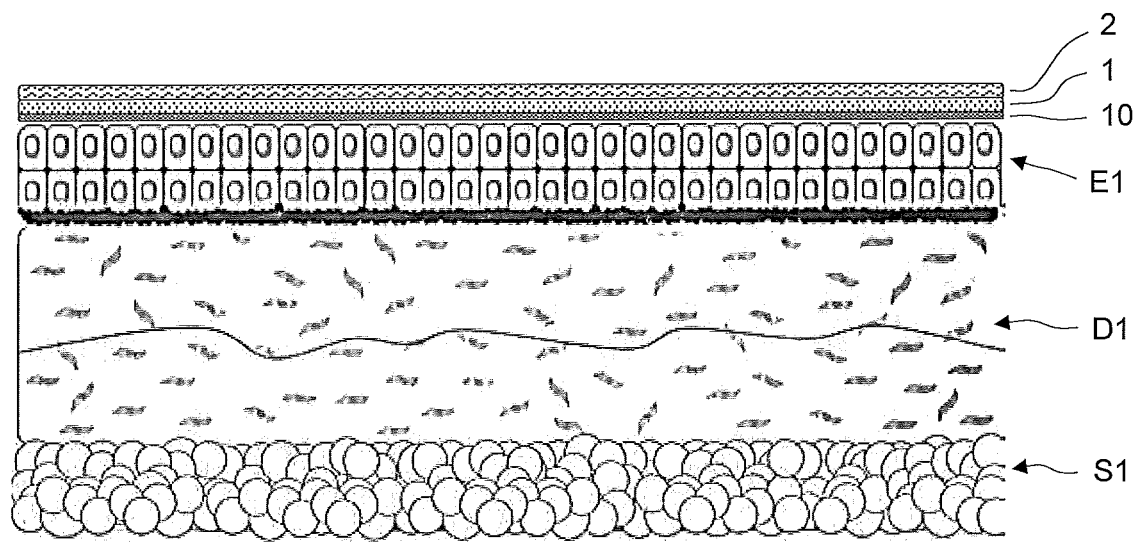
FIG. 2 a sectional image of human skin with epidermis, papillary and reticular dermis and subcutis, wherein an adhesive layer, a first and a second film are applied onto the skin surface in a layered fashion, wherein the first and the second film together represent a film set.

FIG. 2 illustrates a lateral sectional image of the skin with epidermis E1, dermis D1, which consists of a papillary and a reticular dermis, and subcutis S1. Stuck onto the skin is the film set of the first film 1 and the second film 2. Therebetween, the adhesive layer 10 can be seen.

Preferably, the second film 2 has a peel-off means 9 or a tab, for example as a protruding or projecting portion of an outer edge area of the outer portion 2b of the second film 2. The peel-off means 9 or the tab may be an integral component of the second film 2 or a further layer stuck thereon, in order to be able to hold the second film 2 therewith and peel it off from the first film 1.

Figure 3:
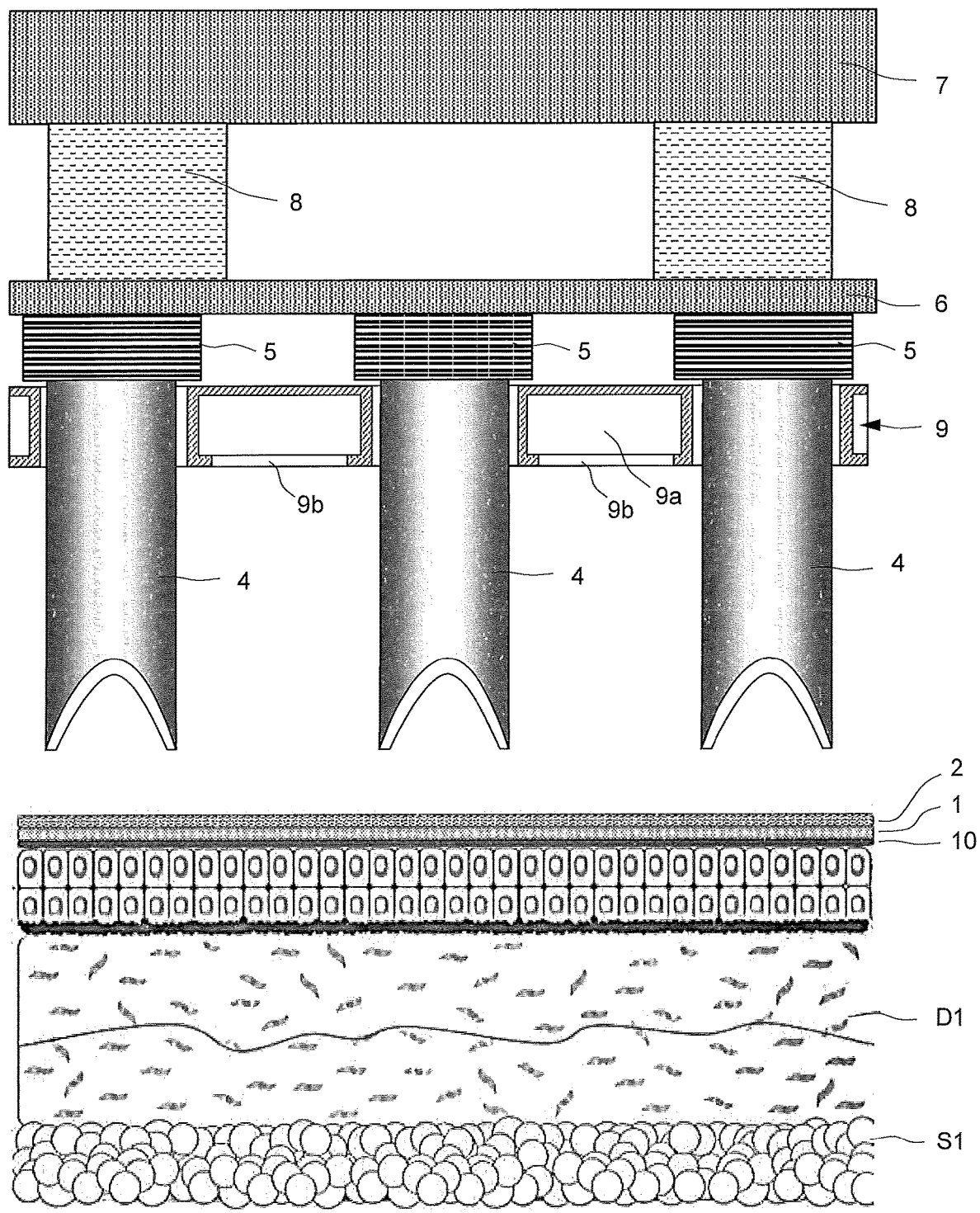
FIG. 3 a side view of the sectional image of FIG. 2 with a cutting device arranged thereabove, comprising a support plate with a plurality of hollow micro-punches, which with one portion are aligned with a cutting edge towards the film set and the skin and with the opposite portion are connected with the support plate via actuators, wherein the support plate is held by a second support via a displacement actuator.

In FIG. 3, the arrangement of the skin with the film set of FIG. 2 stuck thereon is outlined with a preferred cutting device. The preferred cutting device is designed with a support element 6 and a plurality of hollow micro-punches 4, wherein the hollow micro-punches 4 are respectively designed along a longitudinal axis and with a cutting edge at a lower end and; respectively; have a tubular hollow space. The hollow micro-punches 4 may also be referred to as hollow needles. Upon vertical insertion into the skin, the hollow-cylindrical cuts may thus be made. The hollow micro-punches 4 are connected to the support element 6 with an upper portion opposite the cutting edge, so that they form an arrangement of the hollow micro-punches 4 in the form of a matrix in parallel to one another. In that, the hollow micro-punches 4 have such a stiffness, diameter and length, that they extend through the film set down to the predetermined depth and can be pressed into the skin without breaking or bending. For that, the adapter is preferably connected with the skin removal area in a non-slip fashion.

In general, the predetermined depth, with which the cuts are made into the skin, means the depth extending below the first film 1 from the skin surface into the depth of the skin. The thickness of the film set of the first 1 and second film 2 is taken into account when the cutting device makes cuts into the depth of the skin.

Figure 4:
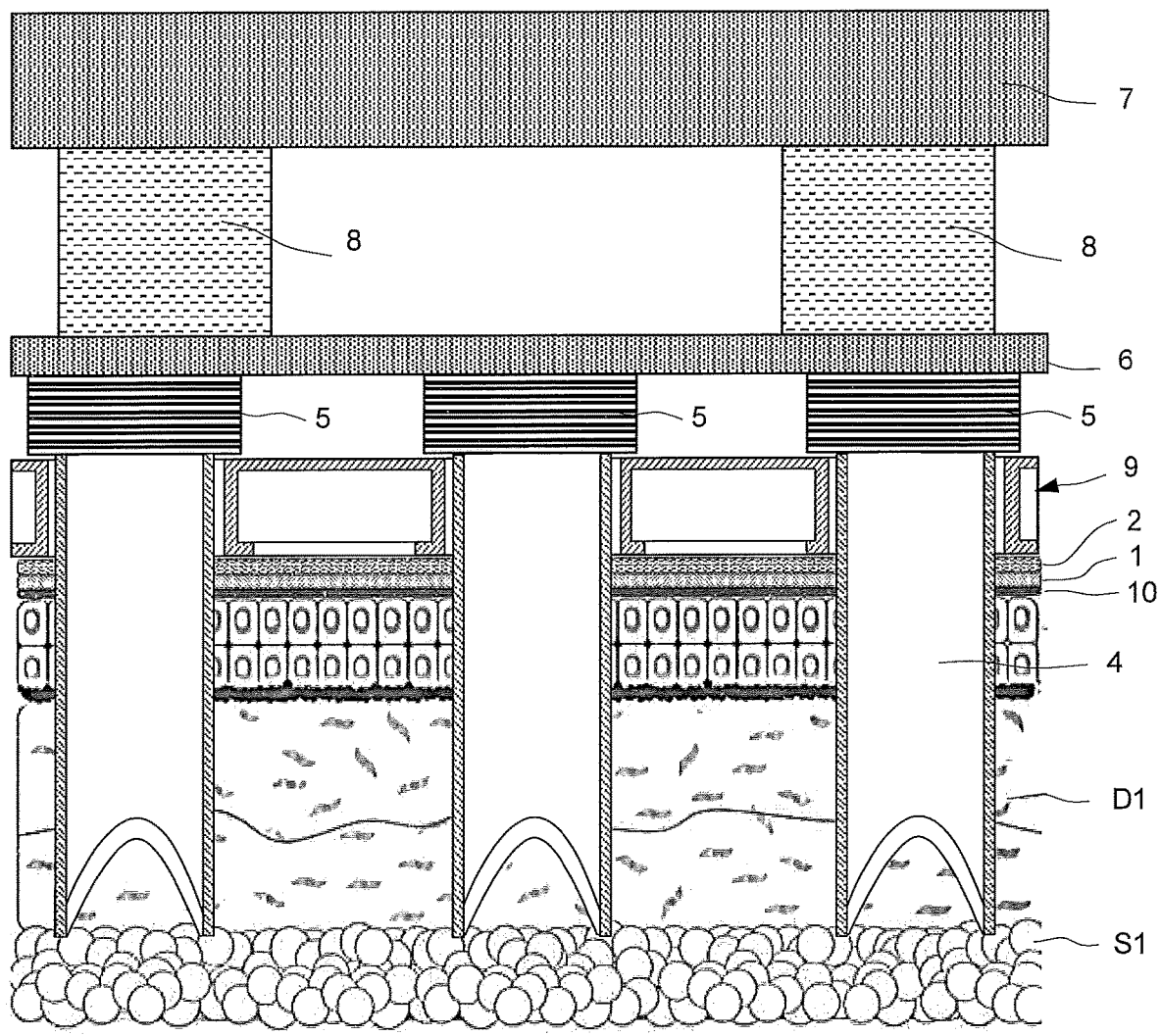
FIG. 4 a side view of the sectional image of FIG. 3, wherein the support plate inserts the hollow micro-punches into the skin down to a predetermined depth, which is preferably located at the end of the dermis, and thereby produces punched full-thickness skin parts.

Thus, the hollow micro-punches 4 cut into the skin with a front portion with a length of the predetermined depth. FIG. 4 illustrates the arrangement of FIG. 3 in a condition, in which the hollow micro-punches 4 are inserted into the skin down to the predetermined depth.

In a front portion with a length of the predetermined depth, which cuts into the skin, the hollow micro-punches 4 preferably have a blade wall thickness of 5-100 µm or 50-200 µm.

In FIGS. 3 and 4, as a preferred embodiment, the support element 6 is additionally held by a second support 7 via a further displacement actuator 8.

Figure 5:
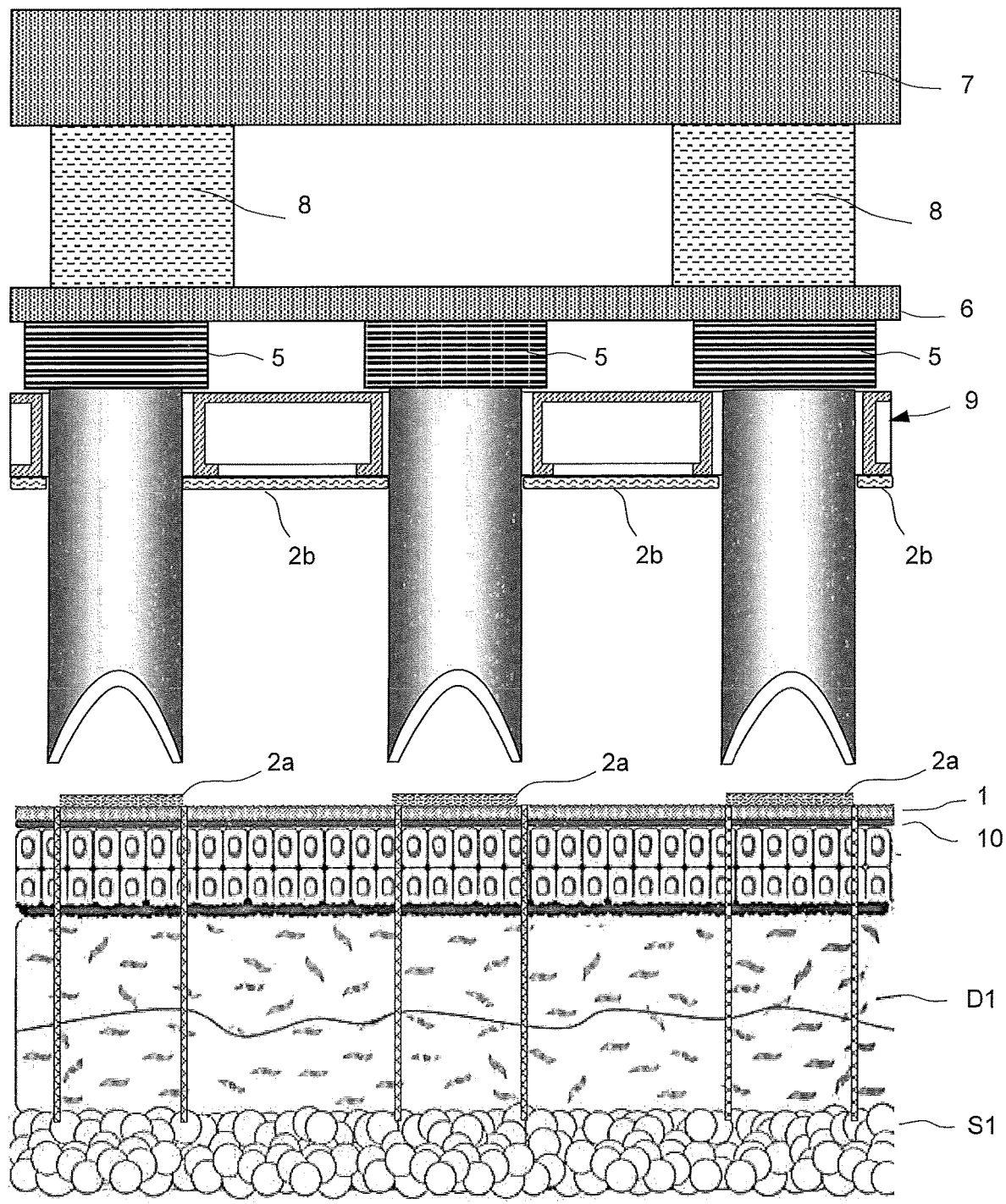
FIG. 5 a side view of the sectional image of FIG. 4, wherein the support plate has extracted the hollow micro-punches again following insertion into the skin and simultaneously peeled off an outer portion of the second film from the first film, wherein the punched full-thickness skin parts only adheres only to the bottom and latterly by friction in the skin.
Figure 6:
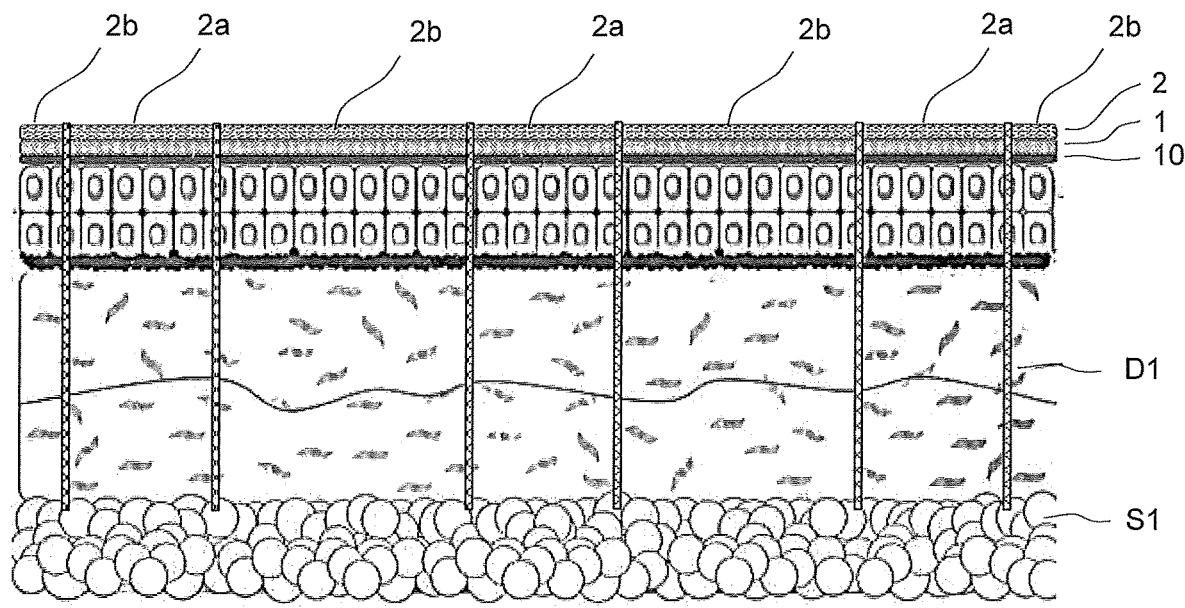
FIG. 6 a lateral sectional image of the skin with the film set thereon according to FIG. 4, wherein the hollow micro-punches have been extracted and the film set with the first and second films is divided by respective cuts into respective inner portions and respectively one outer, remaining portion of the respective first and second films.
Figure 7:
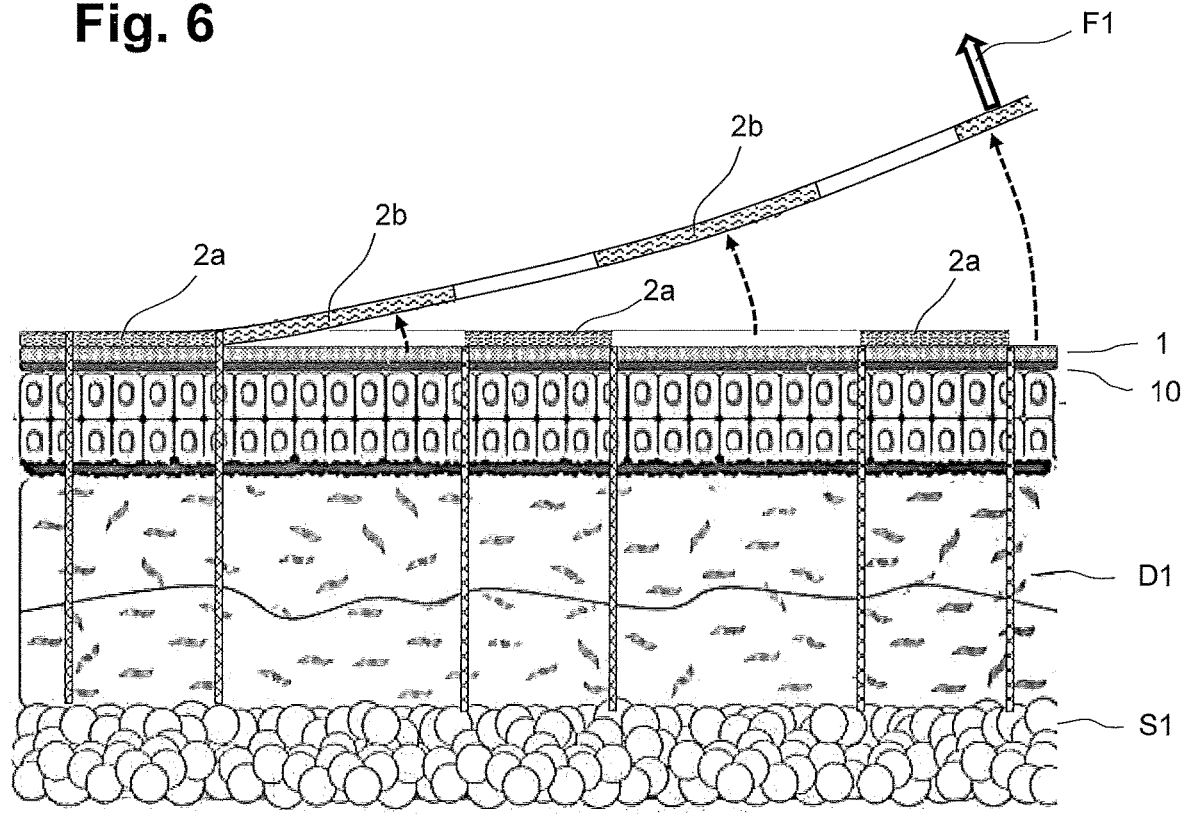
FIG. 7 a lateral sectional image of the skin with the film set of FIG. 6, wherein the outer portion of the second film is partially peeled off from the film set, wherein the inner portions of the second film remain on the first film.

FIG. 5 illustrates the arrangement of FIGS. 3 and 4 in a condition, in which the hollow micro-punches 4 have been extracted from the skin. The peel-off means 9 holds the outer portion 2b of the second film 2 and peels it off, wherein the inner portions 2a of the second film 2 remain on the first film 1. The remaining cuts in the skin are also recognizable. FIG. 6 illustrates the sectional image of the skin with the first 1 and second film 2 following the cutting, wherein the outer portion 2b of the second film 2 has not been peeled off. FIG. 7 illustrates the sectional image of the skin with the first 1 and second film 2 after the cutting, wherein the outer portion 2b of the second film 2 has been partially peeled off at an angle. F1 indicates the peel-off direction.

As an alternative to the hollow micro-punches 4, the cutting device may also comprise a controllable laser with a controllable optical system, in order to generate such a laser beam, which makes the plurality of hollow-cylindrical cuts with the predetermined depth through the film set and into the skin. Preferably, the laser has an optical wavelength in a range of 700-10,000 nm and preferably is an IR laser or a femto-second laser, resp. Preferably, a laser of the state of the art is used, which cuts cold, without causing coagulation or sticking together of cut tissue in the process.

Preferably, the first film 1 and/or the second film 2 are designed with a photo-polymerization layer therebetween, which upon irradiation with the second light radiation enhances the second adhesive strength. The cutting device is preferably designed with a second light source to generate the second light radiation. In case the cutting device comprises the hollow micro-punches 4, the second light radiation is preferably guided through the respective hollow space of the respective hollow micro-punch 4 in the direction of the skin. For example, the second light radiation can be guided from the second light source to the respective hollow spaces through a bundle of light guides. Thereby, the inner portions 2a of the second film 2 are irradiated in a targeted fashion, without irradiating the outer portion 2b of the second film 2.

Figure 16:
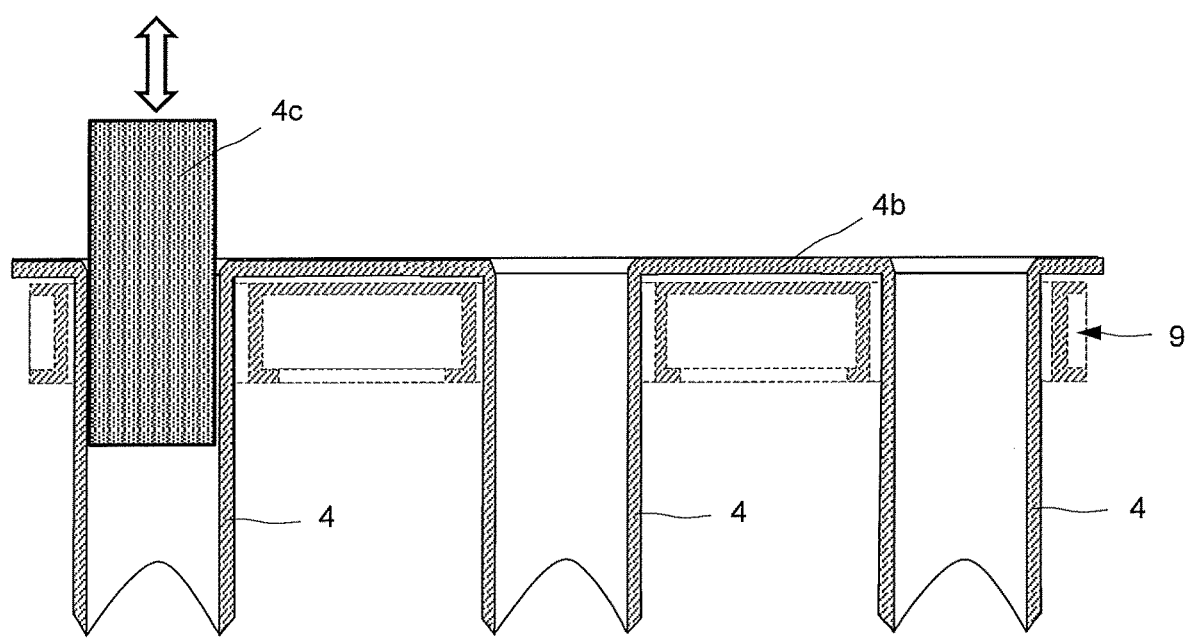
FIG. 16 a side view of part of another preferred cutting device similar to that of FIGS. 3 and 15, wherein in the respective hollow micro-punch, respectively, one mandrel is arranged, which can be moved in the longitudinal direction of the hollow micro-punch; in addition, the cutting edges at a lower end extend in an upward and outward direction.

Preferably, a plurality of mandrels 4c are arranged in the cutting device, as shown in FIG. 16, such that they are movable or displaceable in the respective hollow micro-punches 4. In that, they have an outer diameter, which is slightly smaller than the inner diameter of the hollow micro-punches 4 in order not to get stuck. In that, the mandrels 4c are preferably movable or displaceable in a controlled fashion relative to the hollow micro-punches 4 along the respective longitudinal axis. Controlling is preferably undertaken such that the mandrels 4c release the respective hollow space in the hollow micro-punches 4 upon pressing the cutting device into the skin, so that the respective punched full-thickness skin part 12 can penetrate therein, when the hollow micro-punch is being pressed into the skin. Preferably, the mandrels 4c are advanced up to the skin of the respective punched full-thickness skin part 12 prior to extracting the hollow micro-punches 4 from the skin, should they not be located there already. Upon extraction of the hollow micro-punches 4, the mandrels 4c are held constant relative to the remaining skin and the adapter or are rather advanced a little further into the skin, in order to retain the respective punched full-thickness skin parts 12 in the skin.

Preferably, the cutting device additionally comprises a closed fluid system with a container and a controllable displacement piston, which is controllable by a controller, in order to create a displacement volume. In the fluid system, there is a liquid, which in a first step is displaced into the respective hollow micro-punches 4 at least up to the respective cutting edge by the controller and the displacement piston. In a second and third step, when the hollow micro-punches 4 are inserted into the predetermined depth of the skin and extracted therefrom, the controller controls the displacement piston such that during the second and third step, the level of the liquid in the hollow micro-punches 4 is essentially kept constant relative to the adapter and the skin surface, in order to retain the punched full-thickness skin parts 12 upon extraction of the hollow micro-punches 4 from the skin. The liquid in the hollow micro-punch essentially fulfils the same purpose as the alternative mandrel. The liquid preferably is an aqueous liquid of one of the following components or a mixture thereof: water, salt, adrenaline, local anesthetics, growth factors, vitamins, coenzymes or another pharmaceutical product.

Preferably, the cutting device is designed by the hollow micro-punches 4 being connected with the support element 6 via a respective first actuator 5. In this regard, the respective first actuator 5 is designed and controllable to let the respective hollow micro-punch 4 connected with the first actuator 5 oscillate in the longitudinal direction and/or in a rotational turning movement around the longitudinal axis. The excitation is undertaken with a first oscillation frequency and a first oscillation amplitude in the longitudinal direction and/or a second oscillation frequency and a second oscillation amplitude for the turning movement, which are respectively predetermined such that an adhesion of the punched full-thickness skin parts 12 with the hollow micro-punches 4 is largely avoided. Preferably, the first and second oscillation frequencies lie in a range from 20 kHz to 10 MHz. Preferably, the first and second oscillation amplitudes lie in a range from 1 µm to 300 µm. The actuators 5 preferably are piezo-actuators or electromagnetic actuators.

Preferably, the cutting device is designed such that the support element 6 is connected with a second support via at least one second actuator 8, wherein the at least one second actuator 8 is designed and controllable to move the first support 6 with the hollow micro-punches 4 in the longitudinal direction between a first and a second position. In the first position, the hollow micro-punches 4 are preferably arranged directly above the second film, without penetrating into it. Alternatively, contact or a slight penetration of the hollow micro-punches 4 into the film set is detected by a sensor, wherein the movement of the hollow micro-punches 4 into the skin is stopped at first. In the second position, the hollow micro-punches 4 reach the predetermined depth with their cutting edges. Thereafter, the hollow micro-punches 4 are extracted from the skin and from the film set by the second actuator 8. Preferably, the second actuator 8 is designed to insert the hollow micro-punches 4 into the skin with a first speed and to extract them with a second speed. Preferably, the first speed lies in a range of 10-500 m/s. The hollow micro-punches 4 are preferably accelerated such that an energy to break the skin is overcome, which lies at 19-24 kJ/m$^2$. Preferably, the second speed is 1-100 m/s. The at least one second actuator 8 preferably is a piezo-actuator or electromagnetic actuator.

Preferably, tweezers or forceps or a tab are used to peel off the outer portion 2b from the first film. The outer portion 2b is preferably held by the peel-off means 9 or the tab. Alternatively, the device set may comprise a sucking or adhesive arrangement arranged between the hollow micro-punches 4 above the outer portion 2b of the second film 2 and designed to pull up and peel away the outer portion 2b by sucking it in or adhering thereto. FIG. 3 shows a peel-off device 9, which is interspersed with a hollow space 9a with associated holes 9b, wherein the holes 9b are oriented downwards towards the second portion 2b of the second film. When the outer portion 2b of the second film 2 is to be pulled up, the peel-off device 9 is moved onto the film and then a vacuum is applied to the hollow space, in order to pull up the second portion 2b of the second film 2 and then to be able to peel it off upon moving the peel-off device 9 away from the first film 1. Preferably, the peel-off device 9, as illustrated in FIG. 3, also serves as a stop of the adapter on the film set or the skin.

Figure 14:
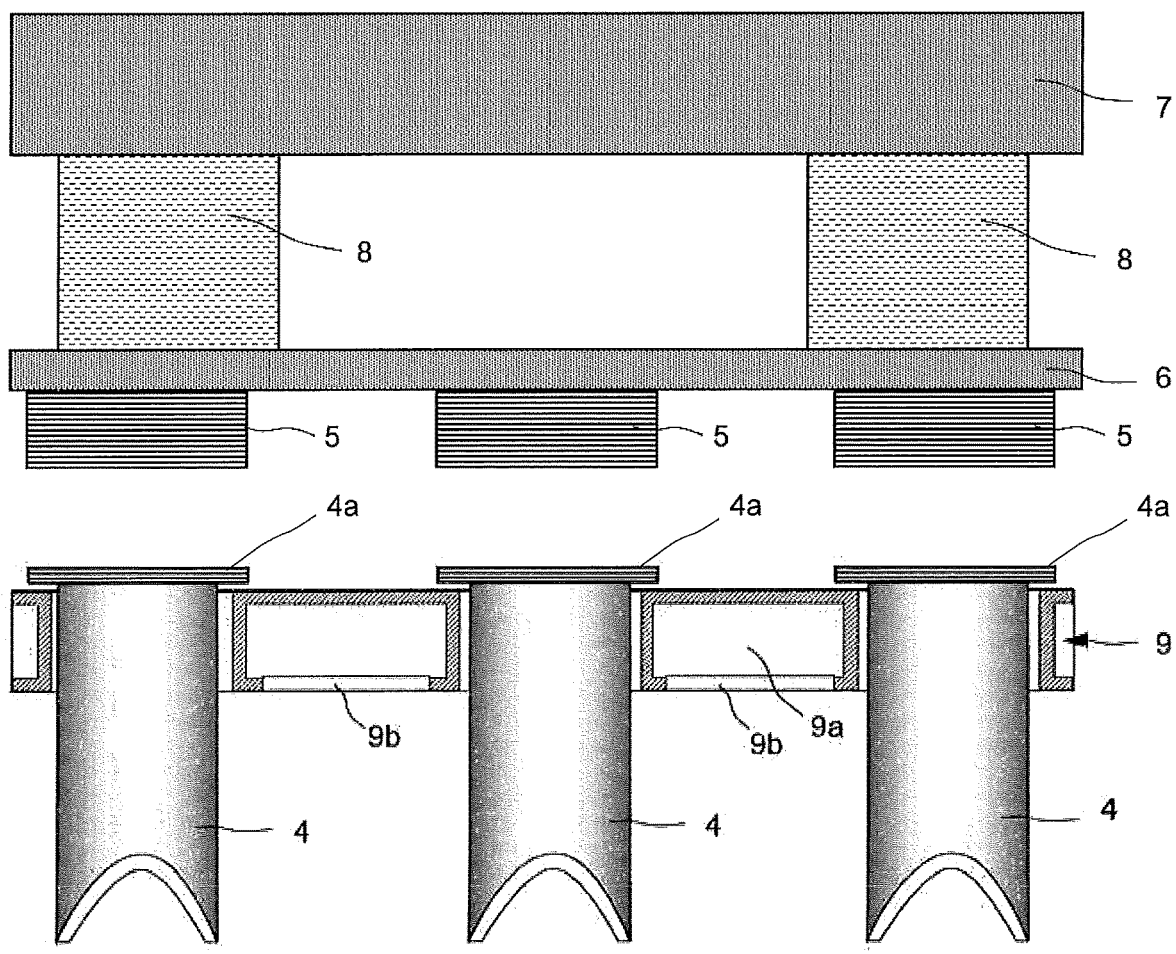
FIG. 14 a side view of the cutting device of FIG. 3, wherein the hollow micro-punches respectively have a contact point at their upper end, which can be connected with a respective counter-contact point at the respective actuator and removed therefrom.

FIG. 14 illustrates a preferred embodiment of the hollow micro-punches 4, which at the respective end opposite the cutting edge are designed with a contact point 4a. The hollow micro-punches 4 can be connected to respective corresponding counter-contact points of the support element 6 via the contact points 4a and detached therefrom. Thus, the plurality of hollow micro-punches 4 can be easily exchanged at the support element 6.

Figure 15:
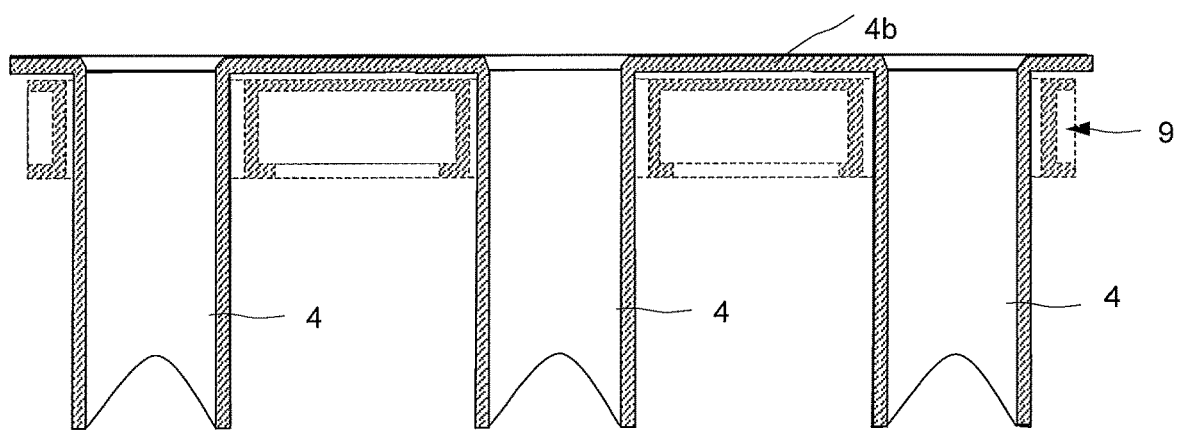
FIG. 15 a side view of part of a preferred cutting device similar to that of FIG. 3, wherein the hollow micro-punches are deep-drawn or stamped-out from a metal sheet with a tear-off edge and form a unit, which can be connected with the support plate.

In a preferred alternative, as illustrated in FIG. 15, the plurality of hollow micro-punches 4 are punched out from a joint sheet metal 4b and inverted, wherein an upper sheet-metal end opposite the cutting edges is two-dimensionally plate-shaped and has holes corresponding with the tubular hollow spaces of the hollow micro-punches 4. The upper sheet-metal end serves as a contact point to a counter-contact point at the support element 6 corresponding therewith. Thereby, the plurality of hollow micro-punches 4 form a unit and can be easily connected with the support element 6 and detached therefrom.

Preferably, the micro-punches 4 essentially consist of the following material or a mixture or a combination thereof: titanium, stainless steel, fiber composite material, biodegradable material, poly-lactide-co-glycolide (PLGA), saccharide, polymers, proteins, spider silk protein, cross-linked and optionally mineralized collagen/gelatin, cellulose.

Preferably, the hollow micro-punches 4 have a monolayer coating, which is designed to achieve as little adhesion with the skin as possible. Preferably, the hollow micro-punches 4 have a coating of the following type or a combination thereof: parylene, ASD (atomic single layer deposition), a hydrophobic coating, a polarized coating having a negatively charged surface, a SAM (self-assembling monolayer) coating, a coating with a fluorine compound or teflon.

Preferably, the cutting device comprises a liquid and a pump associated therewith, which is connected with the hollow spaces of the hollow micro-punches 4 and displaces the liquid with a predetermined amount into the hollow micro-punches 4 or back therefrom. In that, the liquid preferably comprises one or a mixture of the following: water, salt, adrenaline, local anesthetics, growth factors, vitamins, coenzymes, or another pharmaceutical product.

In a preferred embodiment, the third film 3 has at least one perforation, which respectively encloses and forms a break-out area. The at least one perforation is designed such that the respective break-out area of the third film 3 can be broken out therefrom manually or mechanically, once the third film 3 has been adhered to the inner portions 2a of the second film 2 and to the punched full-thickness skin parts 12. The at least one perforation is designed such that the respective break-out area has a diameter of preferably 2-10 mm. Following breaking-out of the at least one break-out area or the film section with the punched full-thickness skin parts 12, the film section can thus be used as a macro-graft, for example for scar treatment, for transplantation into a respectively pre-punched treatment skin area.

Preferably, the first film 1 is designed with a photo-polymerization layer on its first upper side towards the second film 2, which under irradiation with a second light radiation enhances an initial second adhesive strength, until the second adhesive strength is created. Preferably, the second lower side of the second film 2 is designed with a photo-polymerization layer on the side towards the first film 1, which under irradiation with the second light radiation enhances the second adhesive strength.

Preferably, the first film 1 and/or the second film 2 are designed to attenuate light portions with a wavelength shorter than 400 nm by at least 50%.

Preferably, the first film 1 and/or the second film 2 essentially comprise one of the following materials: polymer film, silicone film, polyethylene film, PLGA film.

Preferably, the predetermined thickness of the film set lies in a range of 0.01-1 mm or 1-3 mm.

Preferably, a first thickness of the first film 1 lies in a range of 0.01-0.1 mm or 0.1-1 mm.

Preferably, a second thickness of the second film 2 is at least so large that the third film 3, upon applying it onto the inner portions 2a, after the outer portion 2b has been peeled off, does not touch the first film. Preferably, the second thickness lies in a range of 0.01-0.1 mm or 0.1-0.8 mm.

Preferably, the first film 1, with a second film 2 peeled off, has a surface on the first upper side, which creates no adhesion with the third film 3 or only such an adhesive strength, which is smaller than one tenth of the first adhesive strength.

Preferably, the adhesive 10 is designed as a first adhesive layer and is arranged with the first film 1 on the side towards the skin. Preferably, the adhesive 10 essentially comprises one of the following materials or a mixture thereof: component adhesive, organic and biological polymers or biotin and streptavidin, in which the polymerization is initiated chemically or thermally or by photoactivation or by ionizing radiation.

Preferably, the predetermined depth from the skin surface into the skin lies in a range of 50-500 µm or 0.5-1 mm or 1-3 mm. The predetermined depth essentially extends into the skin down to the lower end of the dermis D1, which is adjacent to the subcutis as a slack and loose displacement layer.

Preferably, the fourth adherence, with which the punched full-thickness skin parts 12 are held in the donor skin, lies in a range of 0.08-4 N/cm$^2$. The first 1, second 2 and third film 3 are set and selected or coated such that the first, second and third adhesive strengths are higher than the fourth adherence.

The hollow micro-punches 4 preferably have an inner diameter of the hollow cylinders, which has a hollow-cylindrical form with an inner diameter of 0.1-0.3 mm or 0.3-0.5 mm or 0.1-1 mm. The hollow cylinder distance is defined as a smallest distance of two adjacent hollow-cylindrical cuts, wherein the hollow cylinder distance lies in a range of 0.1-1 mm or 1-3 mm.

Preferably, the first film 1 and/or the second film 2 and/or the third film 3 are biocompatible. In that, the first film 1 and/or the second film 2 and/or the third film 3 are preferably designed to be biodegradable.

Preferably, the first film 1 and/or the second film 2 are designed with a photo-polymerization layer therebetween, which upon irradiation with the second light radiation enhances the initial second adhesive strength, in order to create the second adhesive strength. The cutting device is designed with a second light source for producing the second light radiation, and the second light radiation is preferably applied onto the second film 2, such that only the inner portions 2a of the second film 2 are irradiated.

Preferably, the third film 3 and the second upper side of the second film 2 are designed to create the third adhesive strength under the influence of the first light radiation hf from the first light source 11. Preferably, the third film 3 is designed to harden under the influence of the first light radiation hf from the first light source 11.

FIGS. 8 and 9 respectively illustrate lateral sectional images of the skin with the first film 1 and the second film 2, from which the outer portion 2b has been peeled off, wherein the third film 3 is applied onto the inner portions 2a and is being irradiated with the first light radiation hf. In FIG. 9, a preferred second adhesive layer 3a is arranged between the inner portions 2a of the second film 2 and the third film 3.

Figure 10:
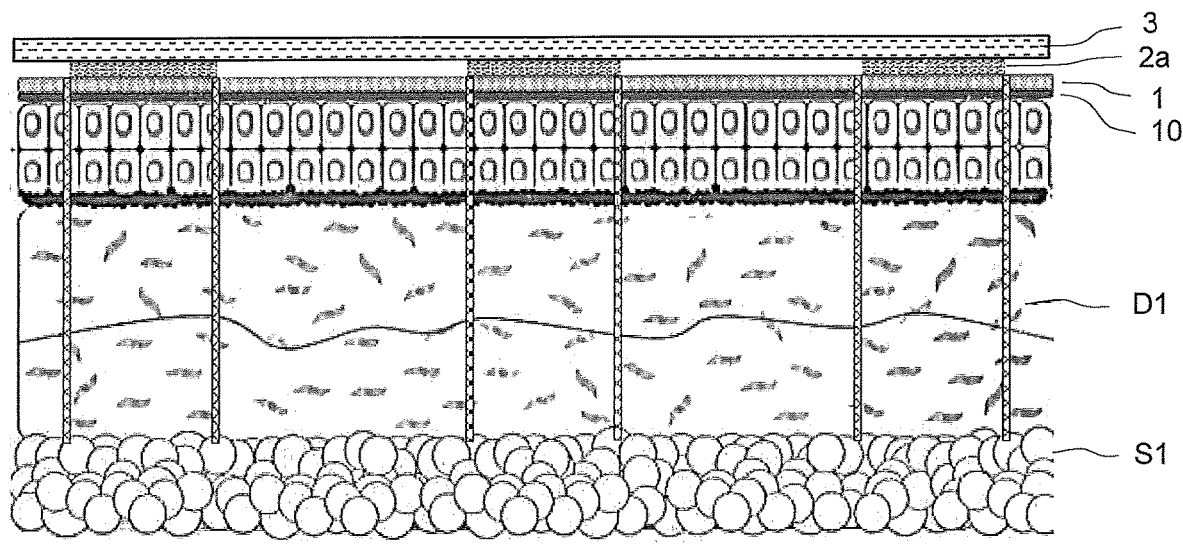
FIG. 10 a lateral sectional image of the skin with the first, second and third films of FIG. 8 following the irradiation.

FIG. 10 shows a lateral sectional image of the skin with the first film 1 stuck thereon by the adhesive 10, wherein the inner portions 2a are stuck onto the first film 1 in the areas of the punched full-thickness skin parts 12, onto which the third film 3 is stuck.

Figure 11:
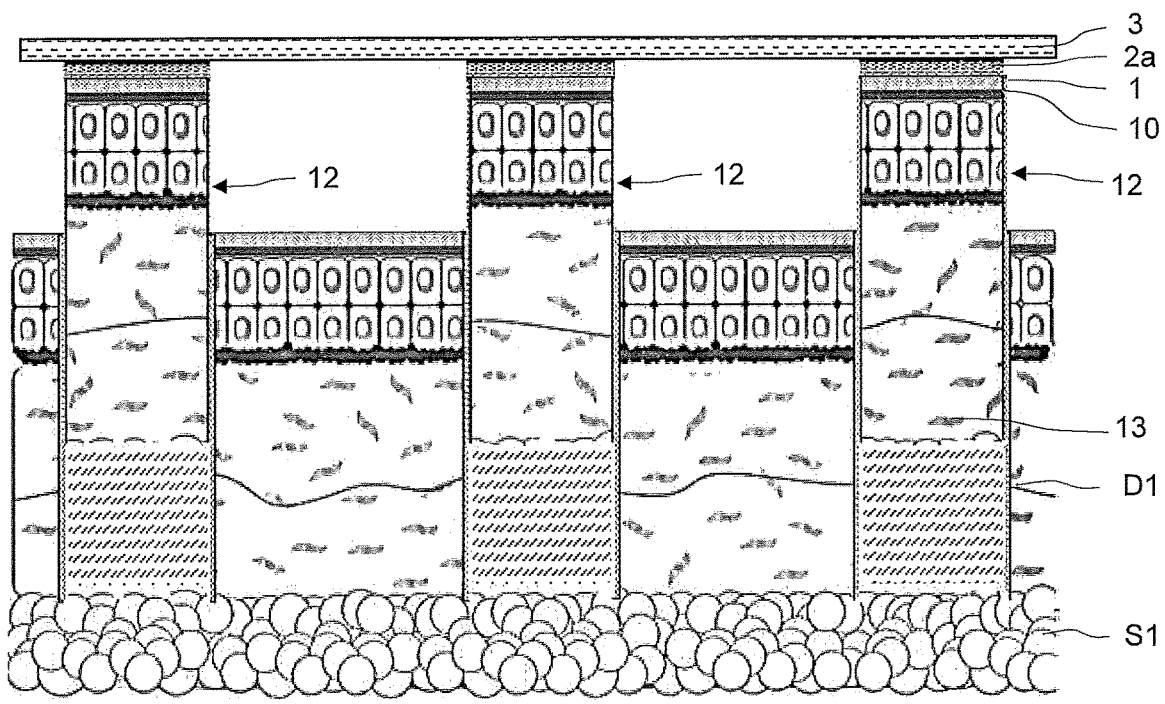
FIG. 11 a lateral sectional image of the skin with the first, second and third films of FIG. 10, wherein the third film is partially extracted with the punched full-thickness skin parts adhering thereto.

FIG. 11 shows the lateral sectional image of the same components as in FIG. 10, however, with the punched full-thickness skin parts 12 partially extracted by the third film 3.

Figure 12:
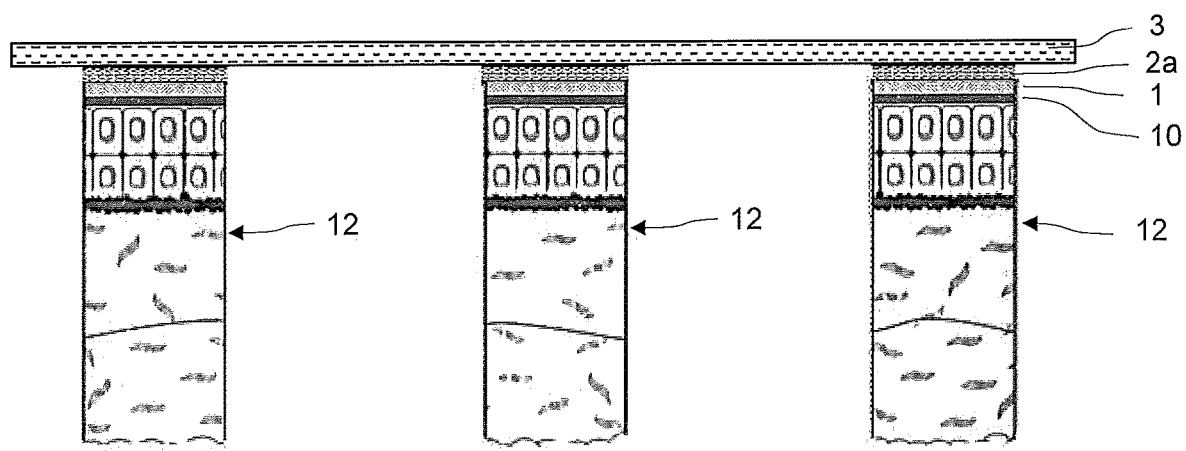
FIG. 12 a lateral sectional image of the third film of FIG. 11, wherein the third film has been extracted with the punched full-thickness skin parts adhering thereto, representing a micro-graft matrix.

FIG. 12 shows the third film 3 with the punched full-thickness skin parts 12 adhering thereto as the micro-graft matrix, after the third film 3 has been completely peeled off from the skin. The micro-graft matrix may now be used for transplantation. Preferably, the micro-graft matrix is wetted with liquid collagen and/or other pharmaceutical products before being transplanted.

Figure 13:
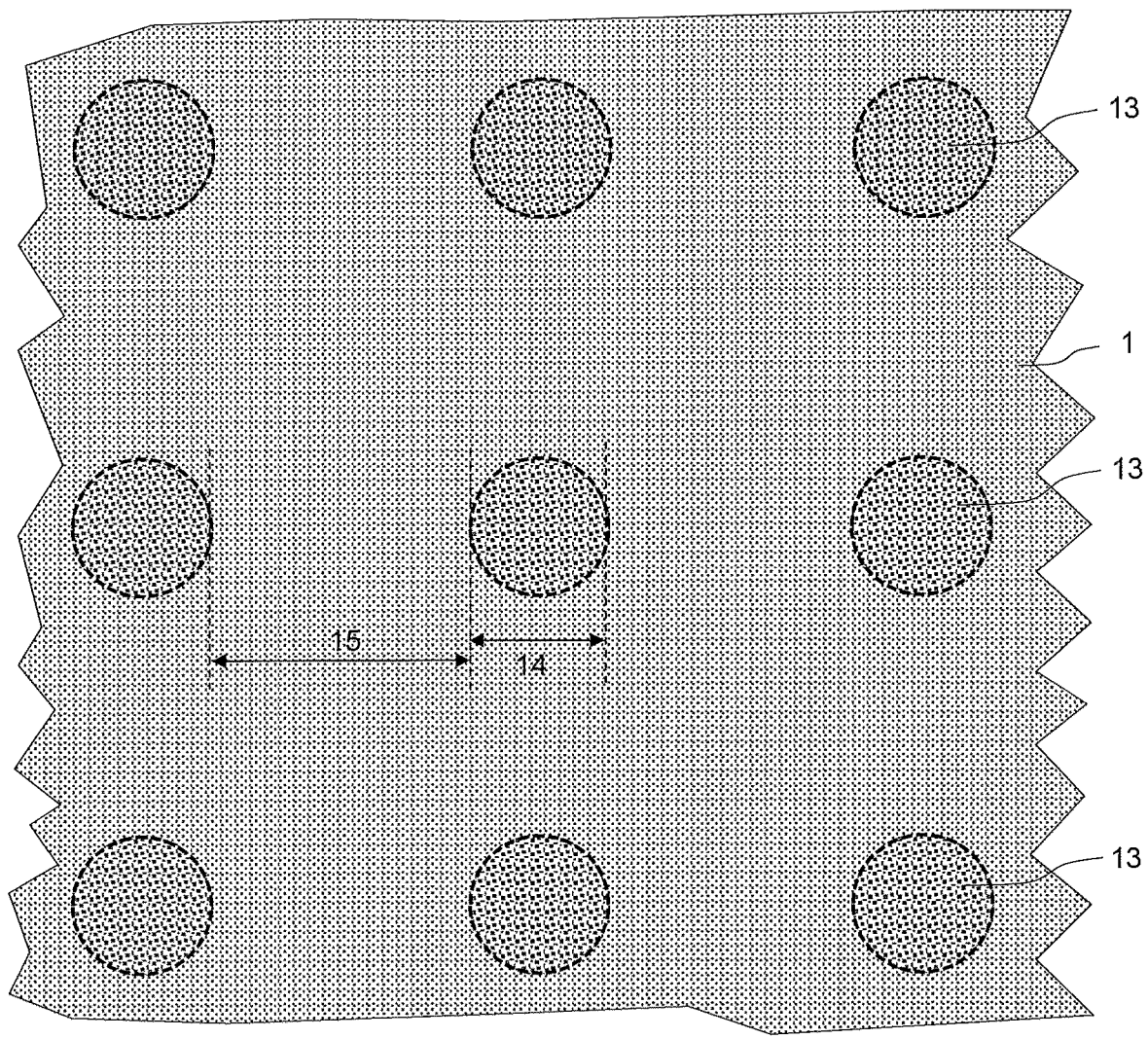
FIG. 13 a top view as a section of a donor skin area, from which the punched full-thickness skin parts have been extracted, wherein remaining cavities can be seen and to which the first film still sticks.

FIG. 13 shows a partial top view of the skin removal area with the first film 1 stuck onto the skin, wherein the outer portion 2b of the second film 2 has been peeled off and the third film 3 with the punched full-thickness skin parts 12 adhering thereto has also been peeled off, so that in those places from which the punched full-thickness skin parts have been extracted, cavities 13 have been created and are visible. The hollow-cylindrical cuts in the skin are recognizable as dashed lines on the skin surface as a cross-section with a respective inner diameter of the hollow cylinder 14, wherein the hollow-cylindrical cuts have a respective hollow cylinder distance 15.

Preferably, the third film 3 has a photoactivatable polymer layer at least on its lower side facing the second upper side of the second film 2, which upon irradiation with the first light radiation hf forms a covalent and/or interlinking bond with the second film 2.

Preferably, the second film 2 has a photoactivatable polymer layer at least on its upper side, which upon irradiation with the first light radiation hf forms a covalent and/or interlinking bond with the third film 3.

Preferably, the third film 3 essentially comprises one of the following materials or a mixture thereof: polymer film, organic polymers, biological polymers.

The first 1, second 2 and third films 3 are preferably designed across the entire skin removal area in a two-dimensional and coplanar fashion.

The adhesive strength of a respective film with a respective adjacent film can be created by respective surface roughnesses and/or by a respective same or inverted polarization of a respective surface. In addition, crosslinking agents can more or less bind the surfaces with one another and create respective adhesive strengths. Such processes and bonds are sufficiently known from the state of the art. In order to reduce adhesion of the third film to the first surface of the first film, for example, nanocoating may be undertaken as well.

An apparatus is also preferred, which detects positions of the inner portions 2a from above and there creates the third adhesive bond following application of the third film 3 in a targeted fashion by a laser light or light application, for example, by welding the inner portions 2a of the second film 2 to the third film 3.

The inventive method for producing the micro-graft matrix with the plurality of punched full-thickness skin parts 12 from skin of the skin removal area comprises the following steps in the sequence indicated:

a) providing
the film set of at least the first film 1 and the second film 2, wherein the first film 1 is designed to be stuck onto the skin with its flat first lower side. The coplanar first upper side opposite the first lower side adheres to the second lower side of the second film 2 in a coplanar fashion with the second adhesive strength, wherein the second film 2 can be peeled off from the first film 1; and
the third film 3 separate from the film set, having a size at least as large as the removal area and being designed, in contact with the second upper side of the second film 2 opposite the second lower side of the second film 2, to create the third adhesive strength, wherein the first, second and third adhesive strengths are set higher than the predetermined fourth adherence;
b) sticking the first lower side of the first film 1 onto the skin with the adhesive 10 therebetween, wherein the first adhesive strength is created between the first lower side of the first film 1 and the skin, which is higher than the second adhesive strength, so that the second film 2 can be peeled off from the first film 1 sticking to the skin;
c) positioning the cutting device with the adapter on the skin removal area, so that, with the adapter above the film set, the predefined distance to the skin underneath is provided.
d) This is followed by the cutting of the plurality of hollow-cylindrical cuts in parallel to one another, which respectively have the inner diameter of the hollow cylinders and one or different hollow cylinder distances from one another, wherein the cuts are made vertical to the film set and down to the predetermined depth in the skin underneath. The plurality of cuts are distributed in the skin removal area in the form of a matrix and the respective cuts have a distance from one another, so that they do not intersect one another.

Thereby, the film set is subdivided into a plurality of inner portions and one respective outer portion. The second film is subdivided into the plurality of inner portions 2a and an outer portion 2b, wherein the inner portions 2a of the second film 2 are located above the respectively cut punched full-thickness skin part 12. The respective inner portion 2a adheres to another inner portion of the first film, which in turn adheres to the respective punched full-thickness skin part 12. The respectively cut punched full-thickness skin part 12 is held in the skin by the skin connection at the respective bottom part towards the subcutis, on the one hand, and by lateral friction of the cylindrical cutting surface, on the other hand, from which the fourth adherence results;
e) peeling off the outer portion 2b of the second film 2 from the first film 1, wherein the inner portions 2a of the second film 2 remain on the first film 1;
f) applying the third film 3 onto the upper sides of the inner portions 2a of the second film 2 and pressing the third film 3 thereon;
g) adhering the third film 3 to the inner portions 2a of the second film 2, wherein a third adhesive strength is created therebetween;
h) peeling off the third film 3 from the skin, wherein the plurality of punched full-thickness skin parts 12 are extracted from the skin as the micro-graft matrix and adhere to the third film 3.

Preferably, adhering of the third film 3 to the inner portions 2a of the second film 2 is undertaken under the influence of the first light radiation hf from the first light source 11.

Preferably, prior to the cutting step, the predetermined depth is determined as that depth, which essentially extends down to the lower end of the dermis D1 and/or to the start of the subcutis.

Preferably, cutting of the hollow-cylindrical cuts into the skin is undertaken by using one of the previously described preferred embodiments of the cutting device.

Preferably, following peeling off of the third film 3, the micro-graft matrix from the skin is wetted or bathed with liquid collagen and/or another pharmaceutical product.

For reasons of clarity, the features "top", "bottom", "upper side", "lower side" shall be understood as relative location information in the vertical direction, as illustrated in the figures. Lateral shall mean horizontal, as illustrated in the Figures. The wording "movable" shall mean that part of a device or a device can be moved or positioned in its position in a controlled fashion.

The specification incorporates by reference the disclosure PCT/EP2018/054404, filed Feb. 22, 2018 and DE 10 2017 106 310.2, filed Mar. 23, 2017.

The present invention is, of course, in no way restricted to the specific disclosure of the specification and drawings, but also encompasses any modifications within the scope of the appended claims.

LIST OF REFERENCE SIGNS

A1 Sweat gland
B1 Split-thickness skin
B2 Full-thickness skin
D1 Dermis
E1 Epidermis
F1 Peel-off direction of the third film
hf Light radiation
S1 Subcutis
T1 Sebaceous gland
1 First film of the film set
2 Second film of the film set
2a Inner portion (of the second film)
2b Outer portion (of the second film)
3 Third film
3a Second adhesive layer
4 Hollow micro-punch (preferably cylindrical tubular—also: micro-blade)
 4a Contact point of the hollow micro-punch
 4b Sheet metal
 4c Mandrel (plunger)
5 Actuator (preferably for longitudinal and turning movement)
 6 Support element
 7 Second support
 8 Displacement actuator (in longitudinal direction)
 9 Peel-off means
 9a Hollow space
 9b Hole
 10 Adhesive
 11 First light source
 12 Punched full-thickness skin part
 13 Cavity 14 Inner diameter of the hollow cylinder
15 Hollow cylinder distance from one another

The invention claimed is:

1. A device set for producing a micro-graft matrix with a plurality of punched full-thickness skin parts (12) from skin of a skin removal area, comprising:
   a film set with a predetermined thickness of at least one first film (1) and one second film (2), wherein the first film (1) is designed to be stuck onto the skin with a flat lower side and to adhere, with an opposite upper side, to a lower side of the second film (2) in a coplanar fashion with a second adhesive strength and to be peelable from one another;
   an adhesive (10) to stick the lower side of the first film (1) onto the skin, wherein a first adhesive strength is created between the lower side of the first film (1) and the skin, which is higher than the second adhesive strength, so that the second film (2) is peelable from the first film (1) sticking to the skin;
   a cutting device with an adapter, which is configured, by pressing the cutting device onto the film set sticking to the skin, to provide a predefined distance to the skin underneath in the skin removal area considering the thickness of the film set, wherein the cutting device is configured to make a plurality of hollow-cylindrical cuts in parallel to one another with respectively one inner diameter of the hollow cylinders and one hollow cylinder distance from one another vertical to the film set and down to a predetermined depth in the skin underneath, so that the plurality of the hollow-cylindrical cuts are made in the skin removal area in the form of a matrix, in order to divide the film set by the hollow-cylindrical cuts into respective inner portions with a respective inner portion (2a) of the second film (2) located above the respectively cut punched full-thickness skin part (12) and into a respective outer portion with an outer portion (2b) of the second film (2); and
   a third film (3) having a size at least as large as the removal area, which is configured, in contact with an upper side of the second film (2) opposite the lower side of the second film (2), to create a third adhesive strength, wherein the first, second and third adhesive strengths are higher than an adherence, holding the punched full-thickness skin parts (12) in the skin.

2. The device set according to claim 1, wherein the cutting device comprises a support element (6) and a plurality of hollow micro-punches (4), respectively, formed along a longitudinal axis and with a cutting edge at a lower end and having a tubular hollow space to make the corresponding hollow-cylindrical cuts, wherein the hollow micro-punches (4) are connected with the support element (6) with an upper portion opposite the cutting edge, such that the hollow micro-punches (4) are arranged in the form of a matrix, wherein the hollow micro-punches (4) have such a stiffness, diameter and length, that they extend through the film set down to the predetermined depth and can be pressed into the skin.

3. The device set according to claim 2, wherein the hollow micro-punches (4), in a front portion with a length of the predetermined depth cutting into the skin, have a blade wall thickness of 10-100 µm or 50-200 µm.

4. The device set according to claim 2, wherein the cutting device includes a second light source to produce a second light radiation, wherein at least one of the first film (1) and the second film (2) comprise a photo-polymerization layer therebetween, wherein the photo-polymerization layer, upon irradiation with the second light radiation enhances the second adhesive strength, and the second light radiation is transmitted such that it travels through the inner hollow space of the respective hollow micro-punch (4) towards the film set and thereby only the inner portions (2a) of the second film (2) are irradiated.

5. The device set according to claim 2, wherein the cutting device comprises a plurality of mandrels (4c) arranged in the respective hollow micro-punches (4), having an outer diameter, which is slightly smaller than the inner diameter of the hollow micro-punches (4) in order not to get stuck, and being controllably movable relative to the hollow micro-punches (4) along the respective longitudinal axis, wherein the mandrels (4c) release the respective hollow space in the hollow micro-punches (4) upon pressing the cutting device into the skin, so that the respective punched full-thickness skin part (12) can penetrate therein and the mandrels (4c) hold the punched full-thickness skin parts (12) on the skin upon extraction of the hollow micro-punches (4) from the skin, and wherein the hollow micro-punches (4) are retracted from the skin and the mandrels (4c) remain on the skin.

6. The device set according to claim 2, wherein the cutting device comprises:
   a closed fluid system with a container;
   a controllable displacement piston controlled by a controller; and
   a liquid, wherein, in a first step, the liquid is displaced by the displacement piston into the respective hollow micro-punches (4) at least up to the respective cutting edge, wherein in a second and third step, when the hollow micro-punches (4) are inserted into the predetermined depth of the skin and extracted therefrom, the controller drives the displacement piston such that, during the second and third step, the level of the liquid in the hollow micro-punches (4) relative to the skin is essentially kept constant to keep the punched full-thickness skin parts (12) pressed back into the skin upon extraction (12) of the hollow micro-punches (4) from the skin, wherein the liquid is an aqueous liquid comprising at least one of water, salt, epinephrine, growth factors, vitamins, coenzymes or another pharmaceutical product.

7. The device set according to claim 2, wherein the cutting device is formed by the hollow micro-punches (4) being connected with the support element (6) via a respective first actuator (5), wherein the respective first actuator (5) is configured and controllable to let the respective hollow micro-punch (4) connected with the first actuator (5) oscillate in a longitudinal direction and/or in a rotational turning movement around the longitudinal axis, wherein a first oscillation frequency and oscillation amplitude in the longitudinal direction and/or a second oscillation frequency and oscillation amplitude for the turning movement are predetermined such that an adhesion of the punched full-thickness skin parts (12) with the hollow micro-punches (4) is substantially avoided.

8. The device set according to claim 7, wherein the first and second oscillation frequencies lie in a range from 20 kHz to 10 MHz, and the first and second oscillation amplitudes lie in a range from 1 µm to 300 µm.

9. The device set according to claim 7, wherein the first actuators (5) are piezo-actuators, electromagnetic actuators, or other actuators.

10. The device set according to claim 2, wherein the cutting device is configured, such that the support element (6) is connected with a second support via at least one second actuator (8), and the at least one second actuator (8)

is configured and controllable to move the first support (6) with the hollow micro-punches (4) in the longitudinal direction between a first and a second position, wherein the hollow micro-punches (4), in the first position, are still arranged above the second film, without penetrating into it, and in the second position, penetrate to the predetermined depth, essentially down to the end of a dermis (D1), wherein the hollow micro-punches (4) are inserted into the skin by the second actuator (8) with a first speed and are extracted therefrom with a second speed.

11. The device set according to claim 10, wherein the second actuators (8) are piezo-actuators, electromagnetic actuators, or other actuators.

12. The device set according to claim 2, further comprising a peel-off means (9) or a tab as a protruding or projecting portion of an outer edge area of the outer portion (2*b*) of the second film (2), wherein the peel-off means (9) or the tab is an integral component of the second film (2) or a further layer stuck thereon to hold the second film (2) thereby and peel the second film (2) off from the first film (1).

13. The device set according to claim 2, further comprising a peel-off means (9) or a tab as a protruding or projecting portion of an outer edge area of the outer portion (2*b*) of the second film (2), wherein the peel-off means (9) is a sucking or adhesive arrangement arranged between the hollow micro-punches (4) above the outer portion (2*b*) of the second film (2) and designed to pull up and peel away the outer portion (2*b*) by sucking it in or adhering thereto.

14. The device set according to claim 2, wherein the plurality of hollow micro-punches (4) each have a contact point (4*a*) at a respective end opposite the cutting edge, wherein each contact point (4*a*) is connected with the support element (6) via respective corresponding counter-contact points, is separable from the support element (6), and is connectable with the support element (6).

15. The device set according to claim 2, wherein the plurality of hollow micro-punches (4) are punched out from a joint sheet metal (4*b*) and inverted, wherein an upper sheet-metal end opposite the cutting edges is two-dimensionally plate-shaped and has holes corresponding with the tubular hollow spaces of the hollow micro-punches (4), wherein the upper sheet-metal end has a contact point to a counter-contact point at the support element (6) corresponding therewith, wherein the contact point is connected with the support element (6) and separable from the support element (6).

16. The device set according to claim 2, wherein the micro-punches (4) comprise at least one of titanium, stainless steel, fiber composite material, biodegradable material, poly-lactide-co-glycolide (PLGA), saccharide, polymers, proteins, spider silk protein, cross-linked and optionally mineralized collagen/gelatin, and cellulose.

17. The device set according to claim 2, wherein the hollow micro-punches (4) have a monolayer coating configured to achieve as little adhesion with the skin as possible.

18. The device set according to claim 2, wherein the hollow micro-punches (4) have a coating comprising at least one of parylene, atomic single layer deposition (ASD), a hydrophobic coating, a polarized coating having a negatively charged surface, a self-assembling monolayer (SAM) coating, and a coating with a fluorine compound or Teflon.

19. The device set according to claim 2, wherein the cutting device comprises a liquid and a pump associated therewith, wherein the pump is connected with the hollow spaces of the hollow micro-punches (4) and displaces the liquid with a predetermined amount into the hollow micro-punches (4) or back therefrom, wherein the liquid comprises at least one of water, salt, epinephrine, growth factors, vitamins, coenzymes, or another pharmaceutical product.

20. The device set according to claim 1, wherein the cutting device includes a laser with an optical system for generating a laser beam that produces the plurality of hollow-cylindrical cuts with the predetermined depth through the film set and into the skin.

21. The device set according to claim 20, wherein the laser has an optical wavelength in a range of 700-10,000 nm.

22. The device set according to claim 20, wherein the laser is an IR laser and/or a femtosecond laser type.

23. The device set according to claim 1, wherein the first film (1) comprises a photo-polymerization layer on the side towards the second film (2), wherein the photo-polymerization layer, under irradiation with a second light radiation, enhances the second adhesive strength.

24. The device set according to claim 1, wherein the second film (2) comprises a photo-polymerization layer on the side towards the first film (1), wherein the photo-polymerization layer, under irradiation with a second light radiation, enhances the second adhesive strength.

25. The device set according to claim 1, wherein at least one of the first film (1) and the second film (2) is configured to attenuate light portions with a wavelength shorter than 400 nm by at least 50%.

26. The device set according to claim 1, wherein the first film (1) and/or the second film (2) essentially consist of a polymer film, a silicone film, a polyethylene film, or a PLGA film.

27. The device set according to claim 1, wherein the predetermined thickness of the film set lies in a range of 0.01-1 mm or 1-3 mm.

28. The device set according to claim 1, wherein a first thickness of the first film (1) lies in a range of 0.01-0.1 mm or 0.1-1 mm.

29. The device set according to claim 1, wherein a second thickness of the second film (2) is at least so large that the third film (3), upon applying it onto the inner portions (2*a*), after the outer portion (2*b*) has been peeled off, does not touch the first film.

30. The device set according to claim 29, wherein the second thickness lies in a range of 0.01-0.1 mm or 0.1-0.8 mm.

31. The device set according to claim 1, wherein the first film (1), with a second film (2) peeled off, has an upper surface opposite the skin that creates an adhesive strength with the third film (3), wherein the adhesive strength with the third film (3) is less than one tenth of the first adhesive strength.

32. The device set according to claim 1, wherein the adhesive (10) is formed as a first adhesive layer and is arranged with the first film (1) on the side towards the skin.

33. The device set according to claim 1, wherein the adhesive (10) at least one of a component adhesive, organic and biological polymers, wherein polymerization is initiated chemically or thermally, by photoactivation, or by ionizing radiation.

34. The device set according to claim 1, wherein the predetermined depth from the skin surface into the skin lies in a range of 50-500 μm, 0.5-1 mm, or 1-3 mm.

35. The device set according to claim 1, wherein the adherence, with which the punched full-thickness skin parts (12) are held in a donor skin, lies in a range of 0.08-4 N/cm$^2$.

36. The device set according to claim 1, wherein the hollow cylinders in the hollow-cylindrical shape have an inner diameter of 0.1-0.3 mm, 0.3-0.5 mm, or 0.1-1 mm.

37. The device set according to claim 1, wherein the hollow cylinder distance is a smallest distance between two adjacent hollow-cylindrical cuts, and wherein the hollow cylinder distance lies in a range of 0.1-1 mm or 1-3 mm.

38. The device set according to claim 1, wherein at least one of the first film (1), the second film (2), and the third film (3) are biocompatible.

39. The device set according to claim 1, wherein at least one of the first film (1), the second film (2), and the third film (3) are biodegradable.

40. The device set according to claim 1, wherein the cutting device is designed with a second light source to generate a second light radiation, wherein the first film (1) and/or the second film (2) are formed with a photo-polymerization layer therebetween, wherein the photo-polymerization layer, upon irradiation with the second light radiation, enhances the second adhesive strength, wherein the second light radiation is generated such that only the inner portions (2a) of the second film (2) are irradiated.

41. The device set according to claim 1, wherein the third film (3) and the upper side of the second film (2) are configured to generate the third adhesive strength under the influence of a first light radiation (hf) from a first light source (11).

42. The device set according to claim 1, wherein the third film (3) is configured to harden under the influence of a first light radiation (hf) from a first light source (11).

43. The device set according to claim 1, wherein the third film (3) has a photoactivatable polymer layer at least on a lower side facing the upper side of the second film (2), wherein the photoactivatable polymer layer, upon irradiation with a first light radiation (hf), forms a covalent and interlinking bond with the second film (2).

44. The device set according to claim 1, wherein the second film (2) has a photoactivatable polymer layer at least on its upper side, wherein the photoactivatable polymer layer, upon irradiation with a first light radiation (hf), forms a covalent and interlinking bond with the third film (3).

45. The device set according to claim 1, wherein the third film (3) comprises at least one of a polymer film, organic polymers, and biological polymers.

* * * * *